(12) United States Patent
Cao et al.

(10) Patent No.: US 9,510,873 B2
(45) Date of Patent: Dec. 6, 2016

(54) GUIDING APPARATUS FOR X-RAY-FREE SCREW PLACEMENT BY SPINAL POSTERIOR APPROACH

(71) Applicant: THE FIRST AFFILIATED HOSPITAL OF NANJING MEDICAL UNIVERSITY, Nanjing, Jiangsu (CN)

(72) Inventors: Xiaojian Cao, Jiangsu (CN); Haijun Li, Jiangsu (CN); Jian Tang, Jiangsu (CN); Lipeng Yu, Jiangsu (CN); Hao Xie, Jiangsu (CN); Lei Yang, Jiangsu (CN)

(73) Assignee: THE FIRST AFFILIATED HOSPITAL OF NANJING MEDICAL UNIVERSITY, Nanjing, Jiangsu (CN)

( * ) Notice: Subject to any disclaimer, the term of this patent is extended or adjusted under 35 U.S.C. 154(b) by 0 days.

(21) Appl. No.: 14/441,116

(22) PCT Filed: Nov. 13, 2013

(86) PCT No.: PCT/CN2013/087030
§ 371 (c)(1),
(2) Date: May 6, 2015

(87) PCT Pub. No.: WO2014/127648
PCT Pub. Date: Aug. 28, 2014

(65) Prior Publication Data
US 2015/0297270 A1 Oct. 22, 2015

(30) Foreign Application Priority Data
Feb. 20, 2013 (CN) .......................... 2013 1 0054303

(51) Int. Cl.
A61B 17/70 (2006.01)
A61B 17/17 (2006.01)
A61B 17/88 (2006.01)

(52) U.S. Cl.
CPC ....... *A61B 17/7076* (2013.01); *A61B 17/1757* (2013.01); *A61B 17/8872* (2013.01)

(58) Field of Classification Search
CPC ...................... A61B 17/7074–17/7082; A61B 17/8875–17/8894; A61B 17/1671; A61B 17/17; A61B 17/1757
See application file for complete search history.

(56) References Cited

U.S. PATENT DOCUMENTS

| 4,722,336 A | * | 2/1988 | Kim | .................... | A61B 17/1703 378/162 |
| 2006/0161168 A1 | * | 7/2006 | Matthys | ............. | A61B 17/1728 606/96 |

(Continued)

FOREIGN PATENT DOCUMENTS

| CN | 2416867 Y | 1/2001 |
| CN | 1317294 A | 10/2001 |

(Continued)

*Primary Examiner* — Eduardo C Robert
*Assistant Examiner* — Michelle C Eckman
(74) *Attorney, Agent, or Firm* — Novick, Kim & Lee, PLLC; Allen Xue

(57) ABSTRACT

A guiding apparatus for x-ray-free screw placement by a spinal posterior approach, comprising an interspinous spacer, a slide scale (1), and an angle-changing rod. The apparatus is simple to operate, easy to grasp, and well accepted by physicians. A reliable effect is provided in screw placement. Significantly reduced X-ray exposure is allowed for patients and medical staff. In a small-incision minimally invasive screw placement operation, even without exposing the spinal ligament, a small spike-like protrusion of a base (2) of the interspinous spacer can ensure accurate inters- (Continued)

pinous positioning across the skin. This is applicable for both minimally invasive and incision surgeries and has a wide range of uses.

3 Claims, 1 Drawing Sheet

(56) References Cited

U.S. PATENT DOCUMENTS

2007/0239168 A1* 10/2007 Kuenzi .............. A61B 17/1728
606/96
2011/0009869 A1* 1/2011 Marino .............. A61B 17/1757
606/87

FOREIGN PATENT DOCUMENTS

| CN | 201157401 Y | 12/2008 |
| CN | 201782814 U | 4/2011 |
| CN | 203089352 U | 7/2013 |

* cited by examiner

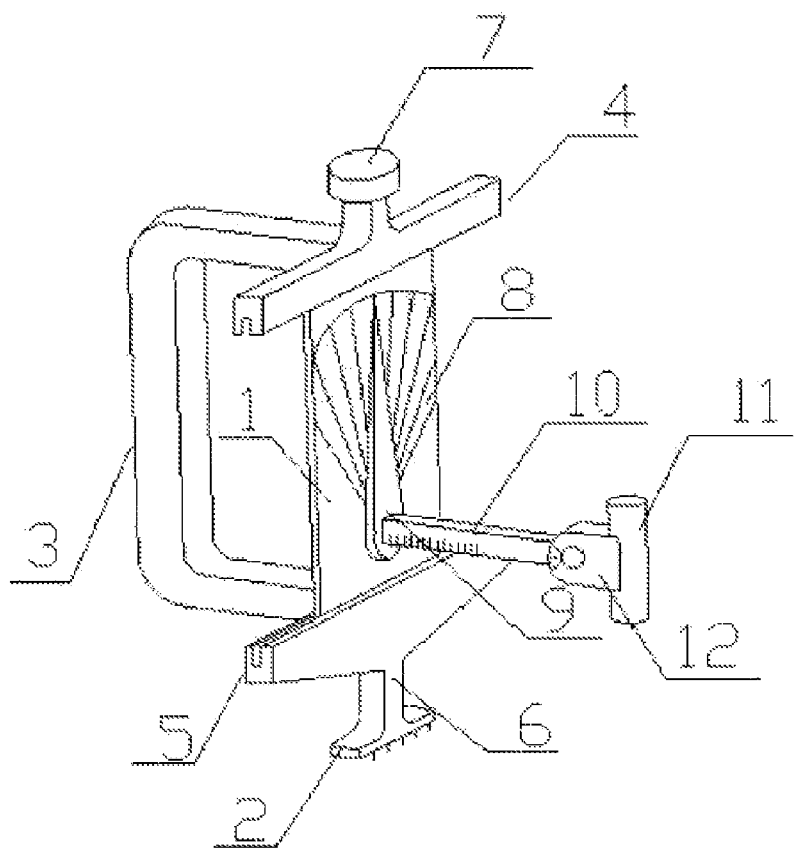

GUIDING APPARATUS FOR X-RAY-FREE SCREW PLACEMENT BY SPINAL POSTERIOR APPROACH

FIELD OF THE INVENTION

The present invention relates to a guiding apparatus for x-ray-free pedicle screw placement via spinal posterior approach and belongs to the field of medical apparatus and instruments.

BACKGROUND OF THE INVENTION

Pedicle screw technique has been developed quickly since its introduction in 1980s and has been widely applied to surgical treatment on affections such as spinal degeneration, spondylolisthesis, spinal stenosis, vertebral fracture, malformation, metastatic tumor of bone, spinal unsteadiness and the like. At present, pedicle screw, one of the internal fixation instruments, is most widely used in spinal surgeries. However, the process of screw placement needs repeated fluoroscopy during actual operations. Particularly, radiation exposure time is apparently increased in minimally invasive operations, such as through a small incision or percutaneous way. Currently, damage of small dose of repeated x-ray exposure to patients and medical care personnel is not clear, but to reduce the x-ray exposure to the patients and medical care personnel during spinal surgeries has become a consensus of all spinal surgeons currently.

Positioning for intra-operative screw placement depends on an X-ray unit presently, which requires repeated intra-operative fluoroscopy and adjustment. During small incision screw placement, more repeated fluoroscopy is needed on the x-ray dose. Therefore, the x-ray exposure to the patients and medical care personnel is apparently prolonged and the operating time is prolonged. Moreover, intra-operative fluoroscopy also increases the probability of surgical incision infection. A latest robot system does not need fluoroscopy during the screw placement process, but a metal positioning screw needs to be embedded before surgery; meanwhile, CT scanning is required. The x-ray exposure to the patients is not reduced and extra pain of placing the positioning screw will be gained. In addition, the robot is expensive, which is used by few hospitals all over the world, and cannot be popularized.

SUMMARY OF THE INVENTION

The objective of the invention is to provide a guiding apparatus that can assist to place a screw accurately, quickly and conveniently during an operation of screw placement via a posterior approach. The operation of screw placement can be carried out without x-rays or under the aid of very few x-rays by using the apparatus, which apparently reduces the x-ray exposure to the patients and medical care personnel.

Technical scheme: a guiding apparatus for x-ray-free screw placement via a posterior approach according to the present invention comprises an interspinous process retainer, a sliding ruler and an angle change-over lever.

The interspinous process retainer comprises a platy base, a C-shaped grip, an upper splint and a lower splint. The sides of the upper splint and the lower splint are respectively and fixedly connected to the two end faces of the C-shaped grip. The upper splint and the lower splint are parallel to each other, and the opposite sides of the upper splint and the lower splint are respectively provided with an upper chute and a lower chute along a length direction thereof. The upper side and the lower side of the sliding ruler are respectively disposed in the upper chute and the lower chute and can slide between the upper splint and the lower splint. The bottom end of the lower splint is fixedly connected to the platy base through a connecting column. The external side of the sliding ruler is provided with an angle dial. The center of the angle dial is provided with a round hole. A rotating wheel is disposed in the round hole. A pointer pointing at the angle dial is disposed on the rotating wheel. A through hole having a square section is disposed in the rotating wheel. An axis of the through hole is overlapped with an axis of the round hole. A symmetric axis of the pointer is overlapped with a symmetric axis of the external end face of the through hole and is vertical to one side of the external end face.

The angle change-over lever comprises a square metal bar and a tubular member matched with the through hole. One end of the metal bar is in plug-in type connection with the through hole so that the rotation of the metal bar keeps consistent with the rotation of the pointer and the metal bar can slide in the through hole. The other end of the metal bar is connected to the tubular member. The tubular member may rotate around the other end of the metal bar through a connecting piece. An axis of the metal bar penetrates through an axle center of the tubular member. A ruler prompting the distance between the axle center of the tubular member and the sliding ruler is disposed on the metal bar. The internal diameter of the tubular member is equal to the diameter of a pedicle screw placement opening cone. The screw placement angle of the opening cone is finally guided through the tubular structure.

The lower splint fixedly connected to the platy base through the connecting column enables the base to present a bilateral valgus design, so that the base is convenient for intraoperative placement and can be particularly convenient to stretch into a subcutaneous portion.

The grip is a side-disposed C-shaped structure that connects the upper splint and the lower splint. The middle portion of the grip is a gripping portion which is mainly for convenient gripping during surgery. Moreover, C-shaped design can avoid sliding of the sliding ruler from being affected by the interference of a connecting structure between the upper splint and the lower splint on the angle change-over lever.

The foregoing technical scheme is further perfected in that the other end of the metal bar is provided with a via hole along a width direction thereof; the tubular member is connected to the via hole through two hinges on a lateral wall of the tubular member; and a prompting scale for prompting rotation angle is carved on the hinge.

The foregoing technical scheme is further perfected in that the lower surface of the platy base is provided with a spike-shaped protrusion for being conveniently fixed on a supraspinous ligament; the top surface of the upper splint is provided with a column-shaped protrusion; after the retainer is correctly disposed during surgery, the protrusion on the base will be fixed on the supraspinous ligament by gently knocking on this portion.

Concrete operations during surgery: Based on sagittal MRI image and side film of the target vertebra, an ideal screw placement angle, an included angle between supraspinous ligament vertical lines and the distance between a pedicle projection outer margin and a spinous process center on a normotopia film of the lumbar vertebra are measured: the first step is to fix the retainer of the guiding apparatus between a spinous process of a screw placement segment of the lumbar vertebra and a spinous process of last segment of the lumbar vertebra after a pedicle screw placement position is preliminarily defined after completion of surgical exposure, i.e.: hold the grip by a hand and use a hammer to gently knock the column-shaped protrusion on the top of the retainer, thus fixing the retainer onto the spinous process stably through the nail-shaped protrusion.

The second step is that an assistant holds the C-shaped grip to stabilize the retainer and a surgeon correctly disposes the angle change-over lever, i.e.: keep the tubular member to be approximately parallel to the pointer, penetrate the metal bar into a square hole slot when the pointer points at zero degree, penetrate the opening cone through the tubular member, and then adjust the direction of the opening cone through properly rotating the tubular member (because the pointer and the tubular member are linked, the pointer will deviate zero degree generally) and adjust the distance between the tubular member and the sliding ruler so as to dispose the remote end of the opening cone onto a position on which the screw is to be placed, move the sliding ruler to make the pointer point at the zero degree in the middle of the angle dial, wherein the direction of the pointer and the direction of the opening cone are consistent at this time, while the direction of the base and the direction of the supraspinous ligament are consistent; when the pointer points at zero degree, it prompts that the pointer and the base are vertical; that is, the opening cone and the supraspinous ligament are vertical; then properly move the sliding ruler to adjust to a correct head declination angle and tail declination angle according to the ideal screw placement angle and the included angle between the supraspinous ligament vertical lines measured before surgery.

The third step is to keep the extroversion angle of the tubular member at zero degree, observe the scale on the angle change-over lever, then further determine whether the selection of the pointer position is proper by contrasting the distance between the pedicle projection outer margin and the spinous process center on the normotopia film of the lumbar vertebra before surgery, wherein a risk of entering a canalisspinalis is prompted if the distance is apparently shorter than that measured before surgery. After the screw placement position is determined, the opening cone can be penetrated after properly controlling the extraversion angle.

Compared with the prior art, the present invention has the advantageous effects that: (1) the operation is easy and simple and the doctor acceptability is good; (2) the screw placement effect is reliable; (3) the price is cheap; (4) the x-ray exposure to sufferers and medical care personnel can be apparently reduced; and (5) in a small incision minimally invasive screw placement operation, the small-spike shaped protrusion on the base can still be accurately positioned between two spinous processes across the skin even if the supraspinous ligament is not exposed; the guiding apparatus for x-ray-free screw placement by spinal posterior approach is both feasible to minimally invasive and incision surgeries and has wide using range.

BRIEF DESCRIPTION OF THE DRAWINGS

FIG. 1 is a structure schematic view of the present invention.

DETAILED DESCRIPTION OF THE PREFERRED EMBODIMENTS

The technical scheme of the present invention will be described in details hereinafter, but the protection scope of the present invention is not limited to the embodiment.

Embodiment 1: as shown in FIG. 1, a guiding apparatus for x-ray-free screw placement by spinal posterior approach comprises an interspinous process retainer, a sliding ruler 1 and an angle change-over lever.

The interspinous process retainer comprises a platy base 2, a C-shaped grip 3, an upper splint 4 and a lower splint 5. The sides of the upper splint 4 and the lower splint 5 are respectively and fixedly connected to the two end faces of the C-shaped grip 3. The upper splint 4 and the lower splint 5 are parallel to each other, and the opposite sides of the upper splint and the lower splint are respectively provided with an upper chute and a lower chute along a length direction thereof. The upper side and the lower side of the sliding ruler 1 are respectively disposed in the upper chute and the lower chute and can slide between the upper splint 4 and the lower splint 5. The bottom end of the lower splint 5 is fixedly connected to the platy base 2 through a connecting column 6. The lower surface of the platy base 2 is provided with a spike-shaped protrusion, and the top surface of the upper splint 4 is provided with a column-shaped protrusion 7.

The external side of the sliding ruler 2 is provided with an angle dial 8. The center of the angle dial 8 is provided with a round hole. A rotating wheel is disposed in the round hole. The rotating wheel can be rotatably clamped in the periphery of the round hole through an annular groove of a lateral wall. A pointer 9 is fixed on the position of the lateral wall of the rotating wheel close to the external end surface. A through hole having a square section is disposed in the rotating wheel. An axis of the through hole is overlapped with an axis of the round hole. A symmetric axis of the pointer 9 is overlapped with a symmetric axis of the external end face of the through hole and is vertical to one side of the external end face. The angle change-over lever comprises a square metal bar 10 matched with the through hole and a tubular member 11 connected with the metal bar 10. The other end of the metal bar 10 is plugged in the through hole so that the rotation of the metal bar 10 keeps consistent with the rotation of the pointer 9 and the metal bar can slide forwards and backwards in the through hole to adjust the distance between the tubular member 11 and the sliding ruler 2. One end of the metal bar 10 is provided with a via hole along a width direction thereof. The tubular member 11 is connected to the via hole through two hinges 12 on the lateral wall of the tubular member. An axis of the metal bar 10 penetrates through the axle center of the tubular member 11. The tubular member 11 can rotate around the other end of the metal bar 10 for adjusting the extraversion angle of the tubular member 11. A prompting scale for prompting rotation angle, i.e. scale for prompting 10 degrees, 15 degrees and 20 degrees, is carved on the hinge 12. A ruler is carved on the metal bar 10 and can prompt the accurate distance between the axle center of the tubular member 11 at the remote end and the sliding ruler 2. The internal diameter of the tubular member 11 is equal to the diameter of a pedicle screw placement opening cone.

As described above, although the present invention has been represented and described with reference to specifically preferred embodiment, it cannot be interpreted as a limit to the present invention itself. Various modifications may be figured out in forms and details without departing from the spirit and range of the present invention defined in the accompanied claims.

The invention claimed is:

1. A guiding apparatus for x-ray-free pedicle screw placement by spinal posterior approach, comprising an interspinous process retainer, a sliding ruler and an angle change-over lever, wherein:

the interspinous process retainer comprises a platy base, a C-shaped grip, an upper splint and a lower splint; the sides of the upper splint and the lower splint are respectively and fixedly connected to the two end faces of the C-shaped grip; the upper splint and the lower splint are parallel to each other, and the opposite sides of the upper splint and the lower splint are respectively provided with an upper chute and a lower chute along a length direction thereof; the upper side and the lower side of the sliding ruler are respectively disposed in the upper chute and the lower chute and can slide between the upper splint and the lower splint; the bottom end of the lower splint is fixedly connected to the platy base through a connecting column; the external side of the sliding ruler is provided with an angle dial; the center of the angle dial is provided with a round hole; a rotating wheel is disposed in the round hole;

a pointer pointing at the angle dial is disposed on the rotating wheel; a through hole having a square section is disposed in the rotating wheel; an axis of the through hole is overlapped with an axis of the round hole; a symmetric axis of the pointer is overlapped with a symmetric axis of the external end face of the through hole and is vertical to one side of the external end face; the angle change-over lever comprises a square metal bar and a tubular member matched with the through hole; one end of the metal bar is in plug-in type connection with the through hole and the other end of the metal bar is connected to the tubular member; the tubular member may rotate around the other end of the metal bar through a connecting piece; an axis of the metal bar penetrates through an axle center of the tubular member; a ruler prompting the distance between the axle center of the tubular member and the sliding ruler is disposed on the metal bar; the internal diameter of the tubular member is equal to the diameter of a pedicle screw placement opening cone.

2. The guiding apparatus for x-ray-free pedicle screw placement by spinal posterior approach according to claim 1, wherein the other end of the metal bar is provided with a via hole along a width direction thereof; the tubular member is connected to the via hole through two hinges on a lateral wall of the tubular member; and a prompting scale for prompting rotation angle is carved on the hinge.

3. The guiding apparatus for x-ray-free pedicle screw placement via a posterior approach according to claim 1, wherein the lower surface of the platy base is provided with a spike-shaped protrusion and the top surface of the upper splint is provided with a column-shaped protrusion.

* * * * *